US009125786B2

United States Patent
Femano et al.

(10) Patent No.: US 9,125,786 B2
(45) Date of Patent: Sep. 8, 2015

(54) METHOD AND DEVICE TO ALLEVIATE CARPAL TUNNEL SYNDROME AND DYSFUNCTIONS OF OTHER SOFT TISSUES

(76) Inventors: Phillip Anthony Femano, Nutley, NJ (US); Michael Frank Zanakis, Palm City, FL (US)

(*) Notice: Subject to any disclaimer, the term of this patent is extended or adjusted under 35 U.S.C. 154(b) by 627 days.

(21) Appl. No.: 13/435,349

(22) Filed: Mar. 30, 2012

(65) Prior Publication Data

US 2012/0253244 A1 Oct. 4, 2012

Related U.S. Application Data

(60) Provisional application No. 61/516,190, filed on Mar. 31, 2011.

(51) Int. Cl.

| | |
|---|---|
| ***A61H 7/00*** | (2006.01) |
| ***A61F 5/01*** | (2006.01) |
| ***A61H 23/02*** | (2006.01) |
| *A61H 15/00* | (2006.01) |

(52) U.S. Cl.

CPC ................ *A61H 7/004* (2013.01); *A61H 23/02* (2013.01); *A61H 2015/0042* (2013.01); *A61H 2201/165* (2013.01); *A61H 2201/1638* (2013.01); *A61H 2201/1642* (2013.01); *A61H 2201/1664* (2013.01); *A61H 2201/1673* (2013.01)

(58) Field of Classification Search

CPC ........... A61H 1/00; A61H 7/00; A63B 23/14; A61F 5/00; A61F 5/013

USPC ........... 601/112–115; 602/21, 62–64; 482/44, 482/46

See application file for complete search history.

(56) References Cited

U.S. PATENT DOCUMENTS

| | | | | | |
|---|---|---|---|---|---|
| 3,088,458 | A | * | 5/1963 | Stewart | 601/122 |
| 3,874,373 | A | * | 4/1975 | Sobel | 601/95 |
| 5,575,761 | A | * | 11/1996 | Hajianpour | 601/48 |
| 6,093,164 | A | * | 7/2000 | Davis et al. | 602/62 |
| 7,238,163 | B1 | * | 7/2007 | Fried et al. | 601/122 |
| 2002/0173738 | A1 | * | 11/2002 | Rogalski | 602/21 |
| 2003/0013580 | A1 | * | 1/2003 | Limonadi | 482/45 |
| 2004/0049136 | A1 | * | 3/2004 | Lin | 601/86 |
| 2004/0260211 | A1 | * | 12/2004 | Maalouf | 601/15 |
| 2007/0055188 | A1 | * | 3/2007 | Avni et al. | 601/151 |
| 2009/0112134 | A1 | * | 4/2009 | Avni | 601/15 |
| 2009/0177129 | A1 | * | 7/2009 | Chan et al. | 601/112 |
| 2009/0197741 | A1 | * | 8/2009 | Poillucci et al. | 482/44 |
| 2009/0221943 | A1 | * | 9/2009 | Burbank et al. | 601/46 |
| 2010/0081973 | A1 | * | 4/2010 | Tsai et al. | 601/134 |
| 2013/0060175 | A1 | * | 3/2013 | Chen | 601/108 |

* cited by examiner

*Primary Examiner* — Justine Yu
*Assistant Examiner* — Christopher Miller
(74) *Attorney, Agent, or Firm* — Porzio, Bromberg & Newman, P.C.

(57) ABSTRACT

The present invention is a device and method to manipulate soft tissues such as tendons using a manipulator that works in conjunction with an orthopaedic device, such as a brace. The manipulator can be an electro-mechanical device. The manipulation can alleviate symptoms of soft tissue dysfunctions such as carpal tunnel syndrome, wrist tenosynovitis and tendonitis, cubital tunnel syndrome, neck tendonitis, plantar fasciitis, and Achilles tendonitis. Manipulation alleviates the inflammation and pressure and the concomitant associated pain and other symptoms of the dysfunction. The manipulation, combined with the orthopaedic aspect of the device, allows the limb to rest and recover between manipulative treatments in a suitably stationary position.

25 Claims, 10 Drawing Sheets

A

B

METHOD AND DEVICE TO ALLEVIATE CARPAL TUNNEL SYNDROME AND DYSFUNCTIONS OF OTHER SOFT TISSUES

CROSS REFERENCE TO RELATED APPLICATION

This application claims the benefit of U.S. Provisional Patent Application No. 61/516,190 filed Mar. 31, 2011, the entirety of which is hereby incorporated by reference into this application.

BACKGROUND OF THE INVENTION

1. Field of the Invention

This invention concerns a device and method to mechanically perform myofascial release and deep tissue massage on tendons and soft tissues in the limbs to achieve relief from conditions such as carpal tunnel syndrome, wrist tenosynovitis and tendonitis, cubital tunnel syndrome, neck tendonitis, plantar fasciitis, Achilles tendonitis, and other soft tissue dysfunctions of the hand, wrist, forearm, leg, ankle, foot, and neck.

2. Background of the Invention

Carpal tunnel syndrome, wrist tenosynovitis and tendonitis, cubital tunnel syndrome, plantar fasciitis, and Achilles tendonitis each describe a condition where tendons and adjacent tissues are inflamed. In tenosynovitis and tendonitis the inflammation is confined to the tendon's sheath or the tendon proper, respectively. There is usually little or no paratendinous involvement. Pain and tenderness over the involved tendon usually results. In carpal tunnel syndrome the inflamed tendons impinge on the median nerve inside the carpal tunnel in the wrist. Similarly, in cubital tunnel syndrome the ulnar nerve is entrapped inside the cubital tunnel of the elbow. Since this is a small confined space, the nerve is effectively pinched or squeezed. The area becomes inflamed and micro-adhesions form between and around the tendons. The result is pain, numbness, tingling, burning and weakness in the hand. In either of these conditions, patients seek treatment, such as, to reduce inflammation, because the pain can be debilitating.

Treating soft tissue dysfunctions such as carpal tunnel syndrome, wrist tenosynovitis and tendonitis, cubital tunnel syndrome, neck tendonitis, plantar fasciitis, and Achilles tendonitis goes beyond alleviating the pain and suffering experienced by patients. Carpal tunnel syndrome is the reason that 3 in 10,000 workers lose job time. The lifetime cost of carpal tunnel syndrome is approximately $30,000 per employee. Cubital tunnel syndrome is less pervasive, yet just as debilitating. While the numbers are not exact, similar burdens on the economy result from tenosynovitis and tendonitis, which are often called repetitive strain injuries or RSIs, plantar fasciitis, and Achilles tendonitis.

Nonsurgical treatment techniques for any of these conditions usually are successful when properly applied. However, such treatment options are quite limited.

Aside from medicines, the most common nonsurgical treatment by far is wrist immobilization and rest. Using an orthopaedic device such as a hand splint or brace is often effective in achieving relief. However, oftentimes such relief is temporary, especially, for instance, if the hand is used too early after a rest period.

When rest is used in combination with certain hand and wrist exercises, the results are better. Such exercises help alleviate inflammation and pain since they promote drainage of interstitial fluid from the affected tissues and breakup of micro-adhesions, which subsequently relieves pressure on sensory nerves.

Oral medications such as nonsteroidal anti-inflammatory drugs or NSAIDs also help to reduce pain, inflammation, and the associated pain. They are commonly used to alleviate the symptoms of carpal tunnel syndrome, wrist tenosynovitis and tendonitis, cubital tunnel syndrome, neck tendonitis, plantar fasciitis, and Achilles tendonitis.

Corticosteroid injections into the inflamed area also help to reduce inflammation, swelling and pain, especially in treating carpal tunnel syndrome. Since corticosteroids are not safe for long term use, injections are limited to only a few during the patient's life.

Surgery aims to alleviate more severe symptoms of carpal tunnel syndrome, wrist tenosynovitis and tendonitis, cubital tunnel syndrome, plantar fasciitis, and Achilles tendonitis. Surgery for tendonitis and tenosynovitis can relieve adhesions and result in pain relief. The outcomes of such surgery are usually fair to good. For alleviating carpal tunnel syndrome, surgery aims to cut the transverse carpal ligament so that the carpal tunnel snaps open. This relieves pressure on the median nerve caused by the inflamed tendons. Surgery for cubital tunnel syndrome usually involves either transposing the ulnar nerve or removing impinging bone.

Carpal tunnel syndrome and cubital tunnel syndrome surgery results are less than perfect. Many times the surgery simply fails to achieve relief. Other times it results in return of symptoms within one to two years. More frequently there are long lasting deficits such as numbness or weakness.

A common technique used by some healthcare practitioners to relieve symptoms of carpal tunnel syndrome, wrist tenosynovitis and tendonitis, cubital tunnel syndrome, neck tendonitis, plantar fasciitis, and Achilles tendonitis is massage. The underlying cause of all of these conditions is inflammation and the resultant micro-adhesions that develop amongst the tissues. Expert massage is an effective way to reduce inflammation and break such adhesions.

Massage techniques aim to move or manipulate tissues in order to achieve a particular result. When properly performed, massage can break adhesions that form when tissues have been damaged. In addition to adhesion breakup, massage makes tissues suppler and easier to glide against adjacent tissues. Finally, massage aids drainage of interstitial fluid through the lymphatic system. This enables waste material to be flushed away from the inflamed area, further enabling healing and reducing swelling.

Combined with massage, joint immobilization is also therapeutic. Maintaining the joint in a neutral or unstressed position allows natural healing processes to transpire unimpeded. This rest period enables the recovery of normal physiology, but if the joint becomes mobile again before healing occurs, more injury can result.

A skilled practitioner such as a massage or physical therapist understands how to move tissues in a three dimensional pattern to maximize the manipulative effect.

On the forearm, as in treating carpal tunnel syndrome, for example, the three dimensional motion produced by a therapist moves the forearm tendons in a forward, backward, side-to-side, and up-and-down direction. Since the tissues are three dimensional structures, only such manipulation can insure thorough movement under the skin to ultimately achieve good results.

One skilled in deep tissue massage techniques may perform this therapy on his or her other arm. It is difficult to achieve good deep tissue massage and myofascial release on your opposite arm since two hands are generally optimal to achieve this. Even when a spouse is instructed to massage the patient, the regimen usually wanes after a few days. This is because most people lack the stamina or skill for a proper deep tissue technique to achieve myofascial release, even when compliance means pain relief for a loved one.

It is desirable to provide a device and method to alleviate carpal tunnel syndrome and dysfunctions of other soft tissues.

SUMMARY OF THE INVENTION

The present invention relates to a device for actively manipulating one or more tendons in the anterior wrist and forearm including a limb engaging portion coupled to a manipulator portion. In one embodiment, the manipulator in use is located adjacent to the anterior wrist and forearm and forms a rigid connection with the limb engaging portion. The manipulator moves against the anterior wrist so as to manipulate the tissue of the anterior wrist. In an alternate embodiment, the manipulator in use is located adjacent the Achilles tendon and/or the sole of the foot so as to respectfully manipulate the Achilles tendon and its adjacent tissues to alleviate Achilles tendonitis and/or the sole of the foot and its adjacent tissues to alleviate plantar fasciitis.

The present invention addresses the problem of relieving symptoms associated with carpal tunnel syndrome, wrist tenosynovitis and tendonitis, cubital tunnel syndrome, neck tendonitis, plantar fasciitis, and Achilles tendonitis. The present invention is an alternative to surgery, drugs, and human-powered manipulative therapy to achieve relief. Since therapeutic massage is effective in alleviating symptoms, the present invention is designed to perform massage automatically, in combination with orthopaedic immobility. In summary, the present invention includes a mechanical means to reproduce therapeutic deep tissue massage motions, in addition to a means of orthopaedic bracing to ultimately achieve tissue healing and alleviation of unpleasant symptoms.

The inventors have found through experimentation and using an embodiment of the present invention, the three dimensional mechanical motions produced over the wrists and forearms are effective for symptomatic relief of wrist tenosynovitis, wrist tendonitis and carpal tunnel syndrome. The mechanical motions preferably are used on subjects who follow a daily treatment regimen. The present invention provides an alternative to invasive surgery and drug-based therapies. The device of the present invention also makes compliance with a deep tissue and myofascial release massage regimen easy for the patient, and can reduce the required duration of massage therapy to achieve the required result.

The inventors have found by experimentation that efficacy is achieved with the embodiment of the invention when the massaging action suitably occurs while the hand and wrist are held in a stationary position, with the hand held slightly flexed. In this way, the inventors have devised a device and method whereby a particular three dimensional massage motion can be imparted to the skin of a region overlying tendinous tissues so that the user experiences deep tissue massage and myofascial release without the need of a human masseuse. The present invention proposes that carpal tunnel syndrome, wrist tenosynovitis and tendonitis, cubital tunnel syndrome, neck tendonitis, plantar fasciitis, Achilles tendonitis, and other bodily dysfunctions of areas of the body with long soft tissue anatomy, especially when tendons and ligaments are involved, can be treated by using a device that engages the affected area and manipulates the soft tissues, and in particular at least one tendon of the affected soft tissue.

Mechanical manipulation can be achieved on a number of areas of the body using manipulation comprising a compact, portable, wearable, and relatively simple electromechanical device of the present invention. The device is combined with an orthopaedic brace primarily for the purpose of fixing the posture of the enclosed body part.

Suitably, the manipulator is adapted to be located near the point where the tendon is close to its insertion or near a bony vertex. For instance, in treating carpal tunnel syndrome the manipulator is located over the anterior wrist and forearm. In another instance, for treating Achilles tendonitis, the manipulator is located over the Achilles tendon near the heel.

Suitably, the manipulator provides, with respect to a tendon, a three dimensional motion. The motion comprises alternating movements laterally or left-to-right, proximally-to-distally, and a superficially-to-deep. This three dimensional motion has been found to be particularly effective at making tendons suppler and seemingly more elastic while encouraging the radial enlargement of the carpal tunnel. It is presumed that if the cross sectional area of the carpal tunnel enlarges relative to the tendons which pass through it, then there will be less compression of the median nerve and reduction of concomitant pain and other symptoms of carpal tunnel syndrome.

In a preferred embodiment of the present invention, the manipulator comprises driving means and one or more manipulating heads. The manipulating head or heads are coupled to the driving means and driven by the driving means in order to provide the manipulation. In this embodiment, the motion of the manipulating head or heads causes manipulation of the affected tissue. In this way the motion of the manipulating head can be adjusted so as to modify the rate and amplitude of each parameter of tissue manipulation.

Preferably, the manipulation, suitably a three dimensional motion, provided by the manipulator, is performed repeatedly. Preferably, the manipulator provides a continuous three dimensional motion. The one or more massaging heads preferably cycle repeatedly at a suitable rate to affect physiological improvement. In the case of carpal tunnel syndrome, for example, the manipulation suitably comprises a three dimensional motion of the one or more manipulating heads and is repeated at a rate of 10 to 100 cycles per minute, and most preferably 30 to 40 cycles per minute. Preferably, the manipulator includes a motor, suitably, a gearmotor for rotating the one or more manipulating heads. Preferably, the device includes a controller for controlling the speed and/or direction of the one or more manipulating heads for the manipulation and massaging of the affected body part.

The three dimensional manipulation can be provided in any suitable manner. For example, rotational or circular motion of the one or more manipulating heads combined with a motion that is substantially perpendicular to the surface of the skin. Another example is lateral motion of the one or more manipulating heads combined with linear (in line with the long axis of the tendon) motion with an up-and-down motion. Another example is planetary motion of the one or more manipulating heads on the skin surface over the tendon combined with a motion that is substantially perpendicular to the surface of the skin.

Suitably, the manipulator comprises at least one manipulating head moving in pattern of motion over the skin. For example, for treating carpal tunnel syndrome, a planetary motion of the head or heads over the anterior forearm surface as well as a motion that is substantially perpendicular to the surface of the skin should be used.

Preferably, each manipulating head comprises rollers. The rollers can be of any configuration so as to provide reduced friction between the roller and skin while the rollers are in motion. Typical configurations of rollers can be wheels, spherical or substantially hemispherical balls, ball bearings, and the like. Preferably, each manipulator head comprises a pair of substantially hemispherical balls spaced on opposite sides of a shaft, such that the balls spin about a central axis over the skin. Preferably, the entire manipulator head assembly also moves cyclically, such that lateral motion, longitudinal motion and superficial-to-deep motion is produced and repeated along a large portion of the skin area and along the tendon length.

The inventors have discovered that the beneficial effects for carpal tunnel syndrome of an embodiment of the present invention is enhanced if the tendons are more exposed on the surface, such as when anterior wrist and forearm flexor tendons protrude when one makes a first or flexes the hand. Accordingly, the device preferably includes a means to extend the tendons and causing them to protrude, thereby rendering improved access by the manipulating head or heads.

In a preferred embodiment, the means to extend the wrist includes a portion of the limb engaging portion when attached to the forearm that enables the wrist to cock up, or flex. This would be preferable in treating the flexor tendons of the hand, such as required in carpal tunnel syndrome or wrist flexor tendonitis. Flexing the hand causes the flexor tendons on the anterior wrist and forearm surface to extend more than that of a relaxed hand. The patient can also hold or grip a ball or a dedicated gripping member of the device to further cause the flexor tendons to elevate.

In contrast to treating carpal tunnel syndrome or wrist flexor tendonitis, in treating wrist extensor tendonitis, for example, the hand can be fixed in the limb engaging portion in order to extend the wrist and thus elevate the extensor tendons of the posterior wrist and forearm. Suitably, the limb engaging portion is located such that the user's wrist bends so as to bring the hand to flex or extend, depending on which tendons (flexors or extensors, respectively) require treatment.

Preferably, in one embodiment, the limb engaging portion comprises a sleeve or cradle which is adapted to be attached to the wrist. Suitably, in this embodiment, the limb engaging portion comprises at least one elongate reinforcing member. For example, the reinforcing member can comprise a splint.

In a preferred embodiment, the limb engaging portion can be jointed so that the forearm is held firmly and the hand and wrist are held firmly. The joint is located between two engaging structures to allow for extension and flexion of the wrist joint. The joint can also provide lateral translation and/or rotation in the wrist joint. Suitably, the joint is adjustable to accommodate any comfortable angle of the wrist relative to the forearm, so that flexor or extensor tendons are maximally exposed by such angularity. Suitably, the joint can be locked into a desired angle by a tightening means, such as a knob.

Preferably, the limb engaging portion in this embodiment supports the wrist during use. More preferably, it is adapted to restrain, preferably substantially immobilize, the wrist in use. Preferably, the limb engaging portion in use extends from the hand and along the forearm. Suitably, the limb engaging portion is adjustable to accommodate different wrist sizes, whether left or right limbs.

In one embodiment, the limb engaging portion comprises an adjustable strap. Suitably, the adjustable strap comprises a hook-and-loop (VELCRO®) fastener. It will be appreciated that other known adjustable fasteners can be used. The limb engaging portion can include a protective inner layer of soft foam or fabric for comfort and to reduce or avoid skin irritation. Preferably, the limb engaging portion can include a protective layer associated with the manipulator so that in use the protective layer is located between the manipulator and the skin. The protective layer can, for example, be a fabric layer. Reducing or avoiding skin irritation is an advantage of a protective layer.

The device of the present invention can include a frame that supports the manipulator and the frame is connected to the limb engaging portion. Preferably, the manipulator can be disengaged from the limb engaging portion. The limb engaging portion which is disengaged from the manipulator is similar to an orthopaedic brace.

Suitably, the device is a portable device, preferably having its own power source. Preferably, the device includes a battery connectable to the manipulator.

Suitably, the device includes a wrist support engaged to a forearm support. Suitably, the wrist support is moveable relative to the forearm support. This allows the hand to be placed in the flexed or extended position relative to the forearm.

In a further aspect, the present invention provides a method of treating or alleviating symptoms of carpal tunnel syndrome, wrist tenosynovitis and tendonitis, cubital tunnel syndrome, neck tendonitis, plantar fasciitis, and Achilles tendonitis, the method comprising the step of manipulating at least one tendon in the affected area, suitably by providing a lateral motion to each tendon with respect to the joint of the affected area. The method can include the step of causing at least one tendon in the affected limb to protrude from the relaxed skin surface.

An embodiment of the present invention is a mechanical device which massages the soft tissues of the wrist reproducing that which is achieved with manually administered deep tissue massage and myofascial release. With the hand and forearm placed supine inside a restraint, the patient, the wrist portion is flexed and locked in place with the limb engaging portion, thereby elevating or flexing the hand relative to the forearm. The manipulator is then affixed to the limb engaging portion, on the anterior aspect, or flexor side, of the forearm.

Massaging motion created by the manipulator is applied to the elevated forearm tendons. This process helps to alleviate pressure on the median nerve and reduce pain. Once massage therapy is complete, the manipulator may be disengaged from the limb engaging portion of the device. The remaining limb engaging portion is an immobilization brace, allowing the wrist joint to rest until the next treatment with the manipulator is required. The device can be made to operate continually or intermittently as needed, in order to provide long-term therapeutic manipulation and thereby alleviate symptoms of carpal tunnel syndrome.

Any one of the aspects of the present invention may be combined with any one or more of the other aspects. Similarly, any one or more of the optional and preferred features of one aspect may apply to any of the other aspects. In particular, features discussed with respect to a method may also apply to a device (for example as a corresponding means) and vice versa.

The invention will be more fully described by reference to the following drawings.

BRIEF DESCRIPTION OF THE DRAWINGS

Embodiments of the invention are described below, by way of example only, with respect to the accompanying drawings, in which.

DETAILED DESCRIPTION OF THE DRAWINGS

Figure 1:
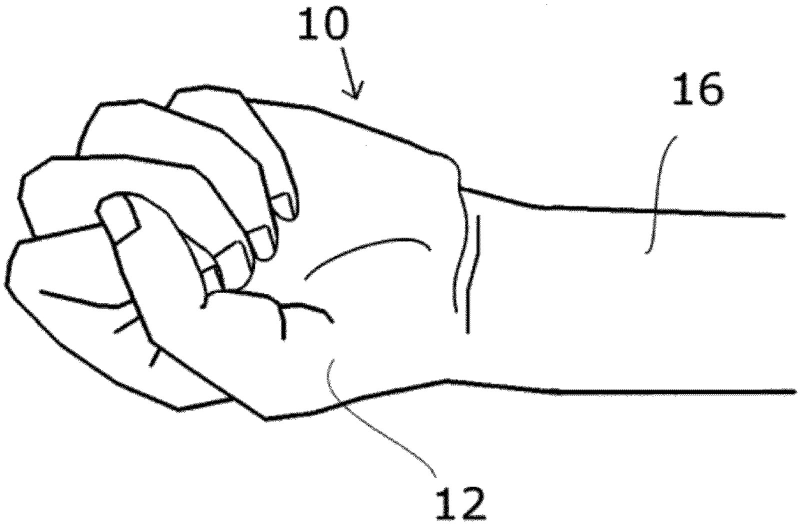
FIG. 1A is a schematic diagram that shows the human hand in a relaxed position.
FIG. 1B is a schematic diagram that shown the human hand in a flexed position which action elevates the flexor tendons in the wrist.
Figure 1:
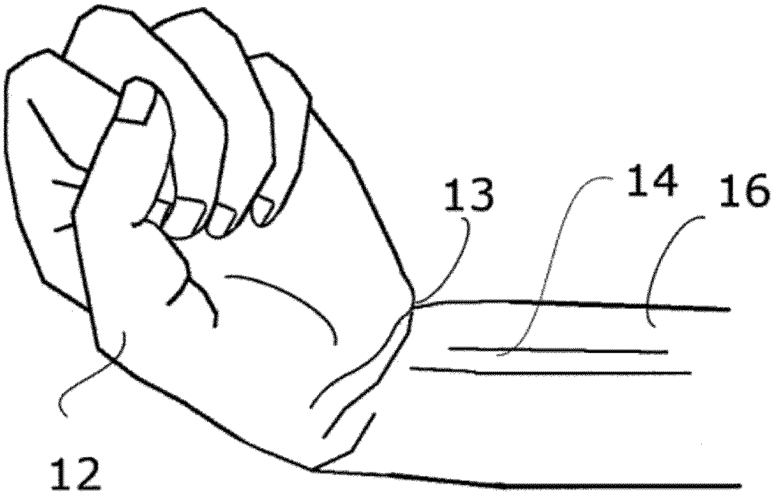

Reference will now be made in greater detail to a preferred embodiment of the invention, an example of which is illustrated in the accompanying drawings. Wherever possible, the same reference numerals will be used throughout the drawings and the description to refer to the same or like parts.

As used herein, the term "anterior" is well known to those skilled in massage therapy but for the purpose of clarification it is intended to mean the part of the body facing anatomically forward. On the arm it is on the same side of the palm. On the leg it is the aspect opposite the foot's sole. The wrist is the anatomical region where the hand and forearm join. The ankle is the anatomical region where the foot and leg join. Reference herein to lateral motion means perpendicular motion with respect to the longitudinal axis of the forearm or leg.

As used herein, the term "posterior" is well known to those skilled in massage therapy but for the purpose of clarification it is intended to mean the part of the body facing anatomically rear-ward while in an erect posture. On the arm it is on the opposite side of the palm. On the foot it is the same side as the foot's sole.

As used herein, the term "proximal" and "distal" are well known to those skilled in massage therapy but for the purpose of clarification are intended to mean "toward the torso" and "away from the torso", respectively.

As used herein, the terms "manipulate" and "manipulation" are well known to those skilled in massage therapy but for the purpose of clarification are intended to mean manual or mechanical movement or displacement of tissue. This can be achieved, for example, by applying pressure and/or motion such as massage, kneading, rubbing etc. to an affected body part, such as the anterior forearm to treat carpal tunnel syndrome.

FIG. 1A depicts human hand 10 with a loosely clenched first 12. FIG. 1B depicts human hand 10 after flexing wrist 13. Wrist flexor tendons 14 are elevated above wrist surface 16 from which they would lie at rest.

Figure 2:
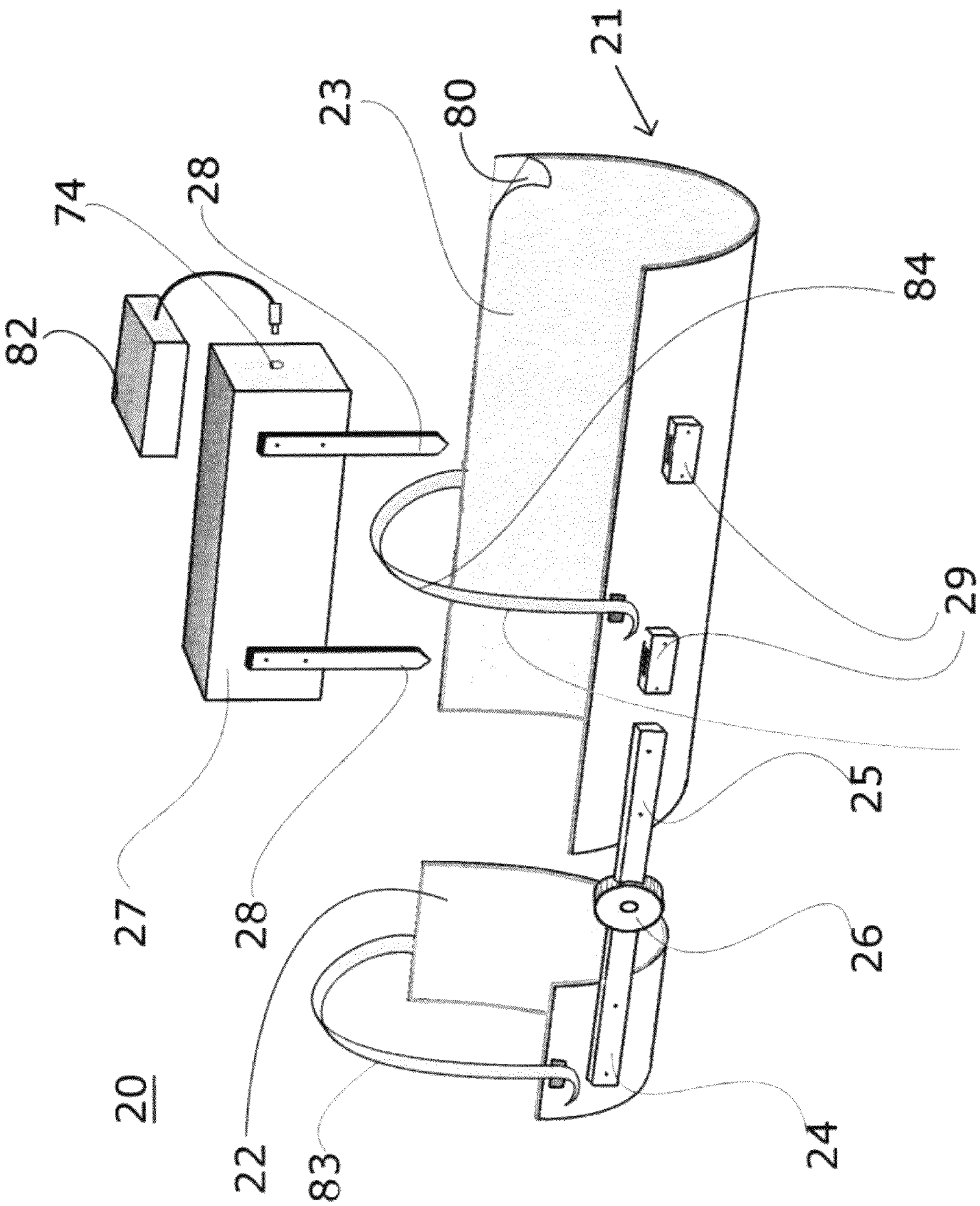
FIG. 2 is a schematic diagram of the device of the present invention, including a limb engaging portion and a manipulator.

FIG. 2 is a schematic diagram of device 20 in accordance with the teachings of the present invention. Device 20 includes limb engaging portion 21. Limb engaging portion 21 includes wrist engaging portion 22 and forearm engaging portion 23. Wrist engaging portion 22 and forearm engaging portion 23 are joined by rigid members 24 and 25. Rigid members 24 and 25 are attached to adjustable locking joint 26. Adjustable locking joint 26 can be one of many types well-known to those skilled in the art of orthotic design. Manipulator 27 is removably attached to limb engaging portion 21. Manipulator 27 is depicted as a box although any enclosure for the internal mechanism is suitable and can be formed in a variety of shapes and sizes. Manipulator 27 has coupling structures 28, for example, as paired bayonet mounts, which, when pushed downward, can penetrate through the matching and paired receivers 29 on limb engaging portion 21. The mating creates a structurally rigid connection between limb engaging portion 21 and manipulator 27. The mounting style is but only one embodiment for similarly mating two such structures. It will be appreciated that a variety of other mounts known to one skilled in the mechanical arts can be used. Straps 83,84 can be affixed to limb engaging portion 21 of device 20 to immobilize a user's arm, hand or wrist in the device. The straps can include hook-and-loop (VELCRO®), and such strapping methods as are common in the field of orthopaedic immobilization. Other alternative restraining means can be employed, such as a clamshell design with mechanical, zipper, or magnetic fastener or any other means that is known to one skilled in the art. Power to the manipulator can be provided by wall current (e.g., via a transformer in the case of a DC gearmotor) when an electrical plug is inserted into jack 74. Alternatively, battery pack 82 can be used to fasten to manipulator 27 to provide power through jack 74 or by another electrical connecting means to the manipulator. In order to minimize skin irritation, device 10 can contain a protective layer 80 as either integral with limb engaging portion 21 or manipulator 27. For example, protective layer 80 can be foam or fabric. Protective layer 80 serves as a protective barrier and to control friction between the massaging heads and the user's skin surface.

Figure 3:
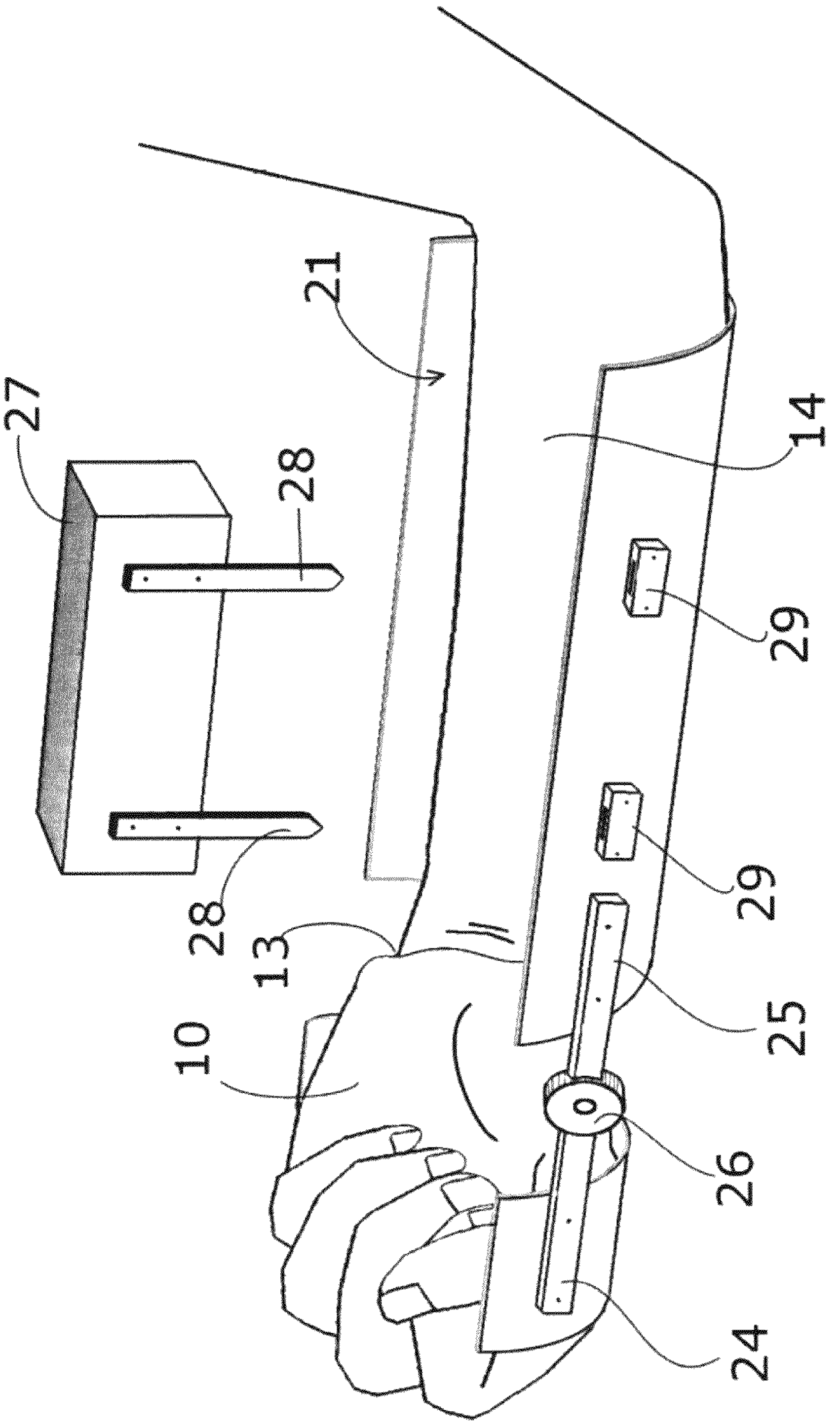
FIG. 3 is a schematic diagram that shows the device located on the wrist and forearm of a user.

FIG. 3 is similar to FIG. 2 but depicts a person using device 20. User's hand 10, wrist 13 and forearm 14 is received in device 20. This embodiment can be used to treat carpal tunnel syndrome or flexor tendonitis of the wrist and forearm. The immobilization straps are not shown in FIG. 2.

Figure 4A:
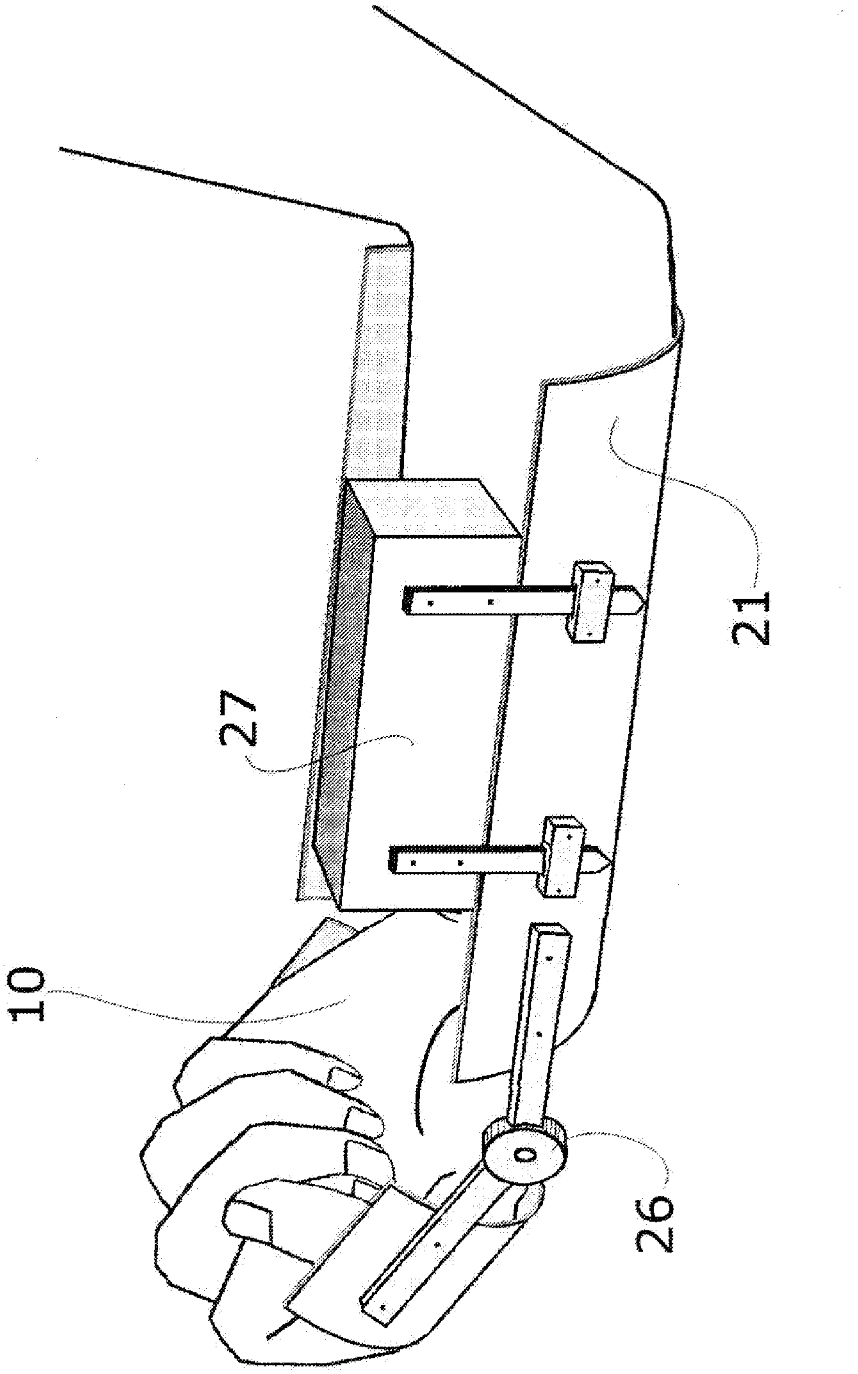
FIG. 4A is a schematic diagram that shows the device located on the wrist and forearm of a user, with the manipulator portion affixed to the limb engaging portion. The limb engaging portion includes a wrist support that is angled relative to the limb engaging portion so that the hand is flexed, thereby elevating the wrist flexor tendons from their resting position at the surface of the forearm.

FIG. 4A is similar to FIG. 3 but the user has flexed his or her hand 10 and locked locking joint 26 to hold that particular angle of flexion. Manipulator 27 also is locked into limb engaging portion 21. This now enables the user to receive massage therapy from manipulator 27 while his or her hand is immobilized in limb engaging portion 21. The immobilization straps are not shown in FIG. 4. Once massage therapy has completed, the user can remove manipulator 27 and still wear limb engaging portion 21 to allow hand 10 to rest and recover for as long as desired. A pronounced protrusion of the forearm flexor tendons can be achieved if the user creates a gripping force with first 12, or grips an object to achieve the same effect. Such a gripped object is not shown in this depiction.

Figure 4B:
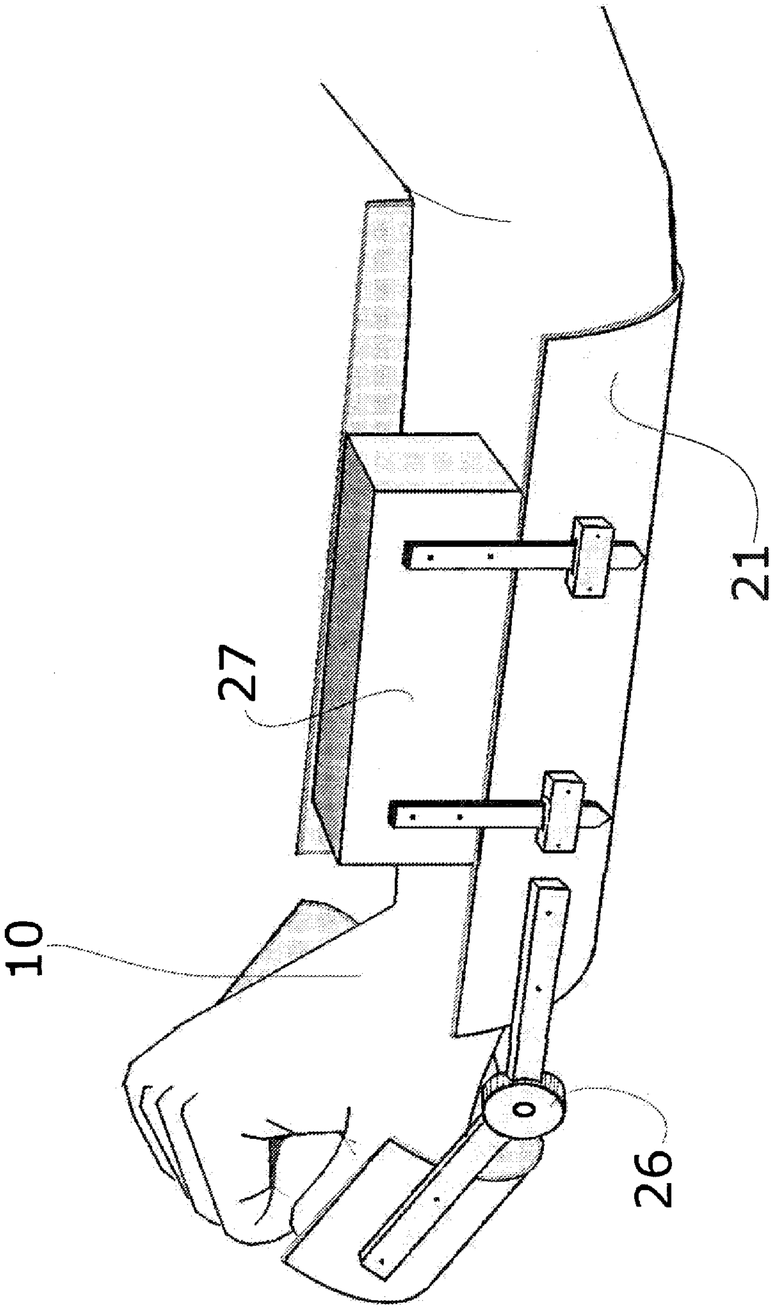
FIG. 4B is a schematic diagram that shows the device located on the wrist and forearm of a user, for the purpose of massaging the extensor tendons of the forearm. The manipulator portion is affixed to the limb engaging portion. The limb engaging portion includes a wrist support that is angled relative to the limb engaging portion so that the hand is extended, thereby elevating the wrist extensor tendons from their resting position at the surface of the forearm.

FIG. 4B depicts the hand and wrist in the device where the extensor tendons of the forearm are being treated. Manipulator 27 is locked into the limb engaging portion 21. This now enables the user to receive massage therapy from manipulator 27 while his or her hand is immobilized in limb engaging portion 21. A pronounced protrusion of the forearm extensor tendons can be achieved by such extension of the hand.

The immobilization straps are not shown in FIG. 4B.

Figure 5:
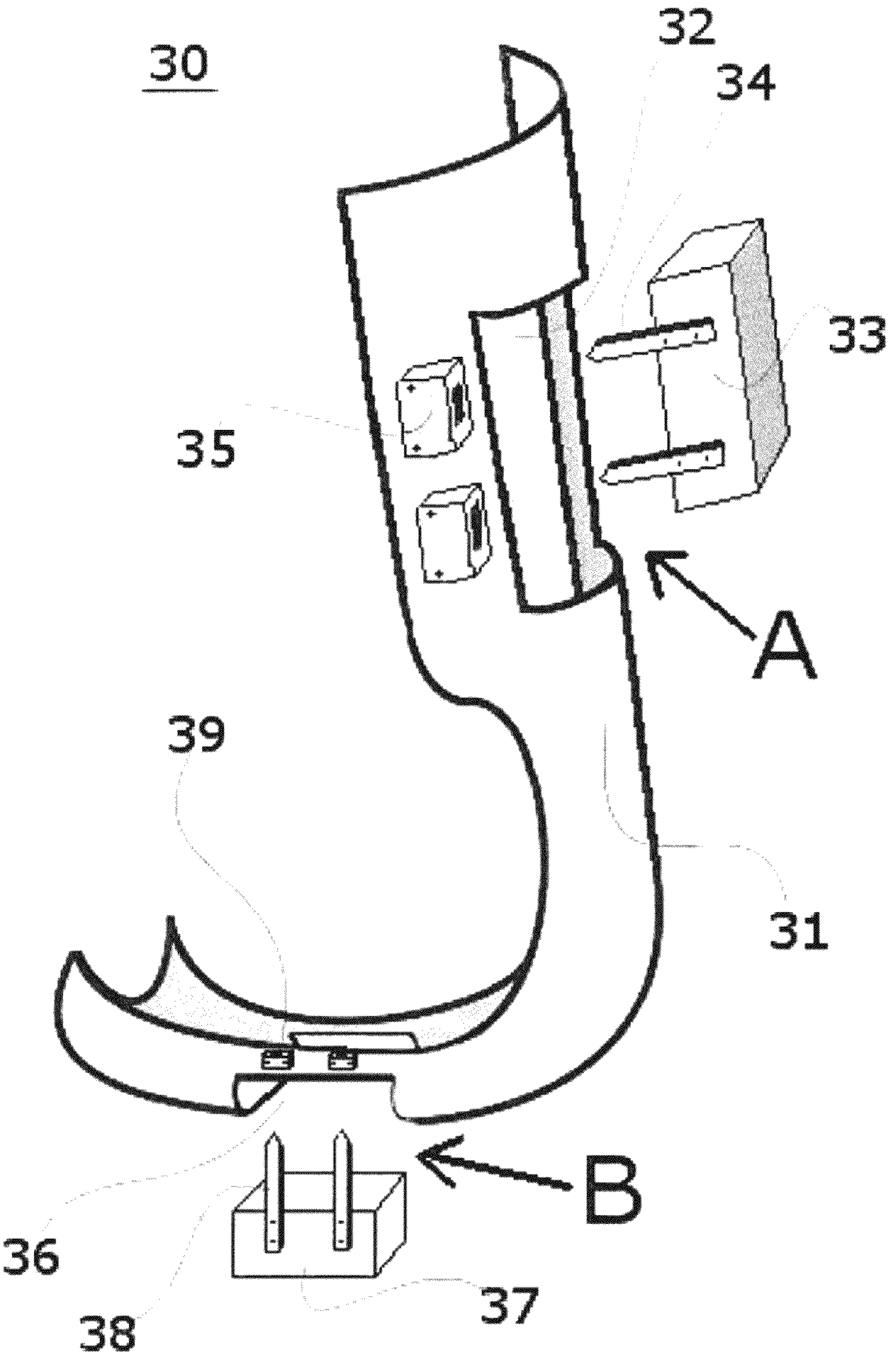
FIG. 5 is a schematic diagram that shows the manipulator above the skin surface of the ankle and foot or the calf.
Figure 6:
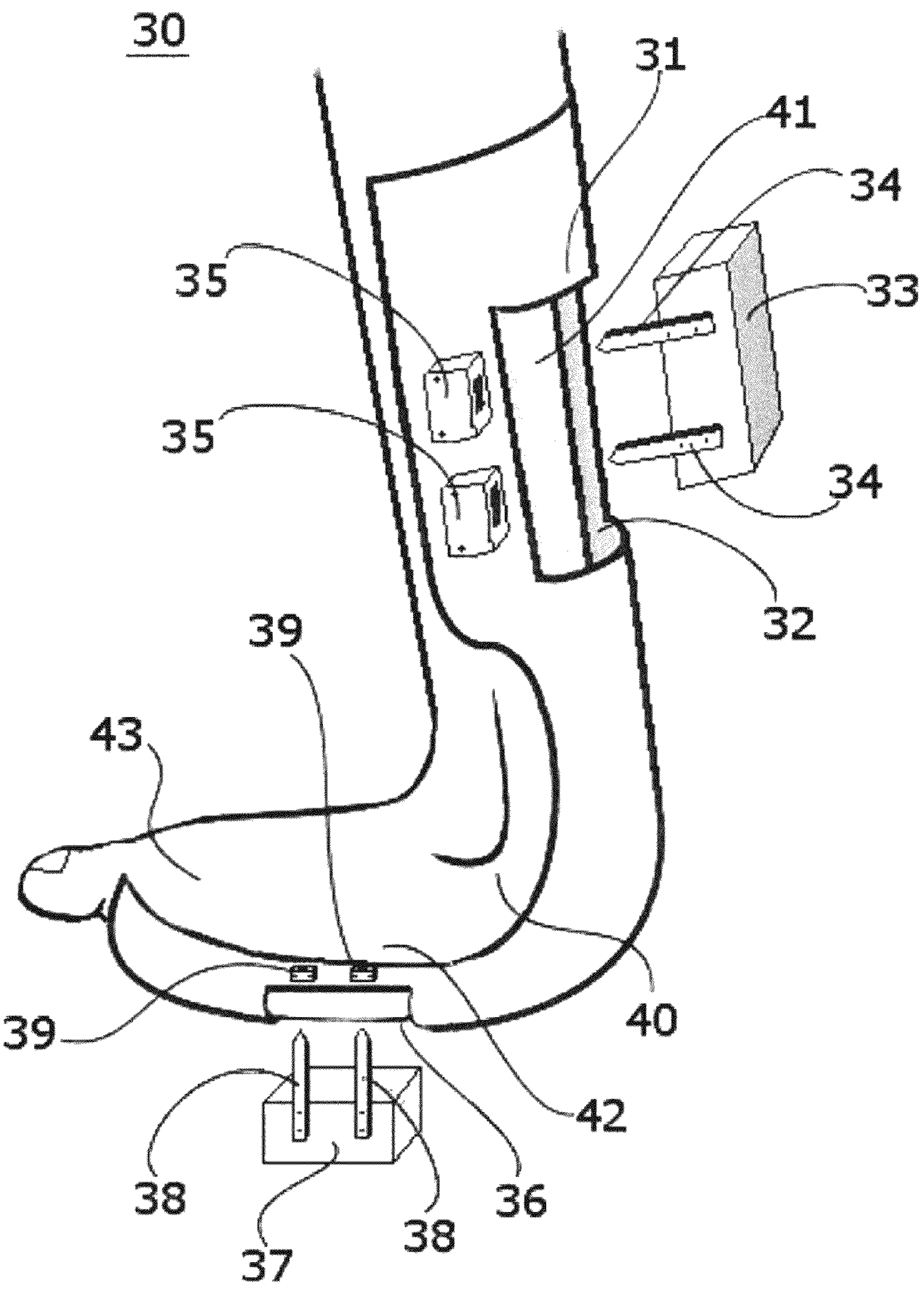
FIG. 6 is a schematic diagram that shows the manipulator portion applied to the foot and ankle. The limb engaging portion is similar to a foot-ankle orthosis and for simplicity and brevity, two embodiments are shown depicting the treatment of either Achilles tendonitis (A) or plantar fasciitis (B).
Figure 7:
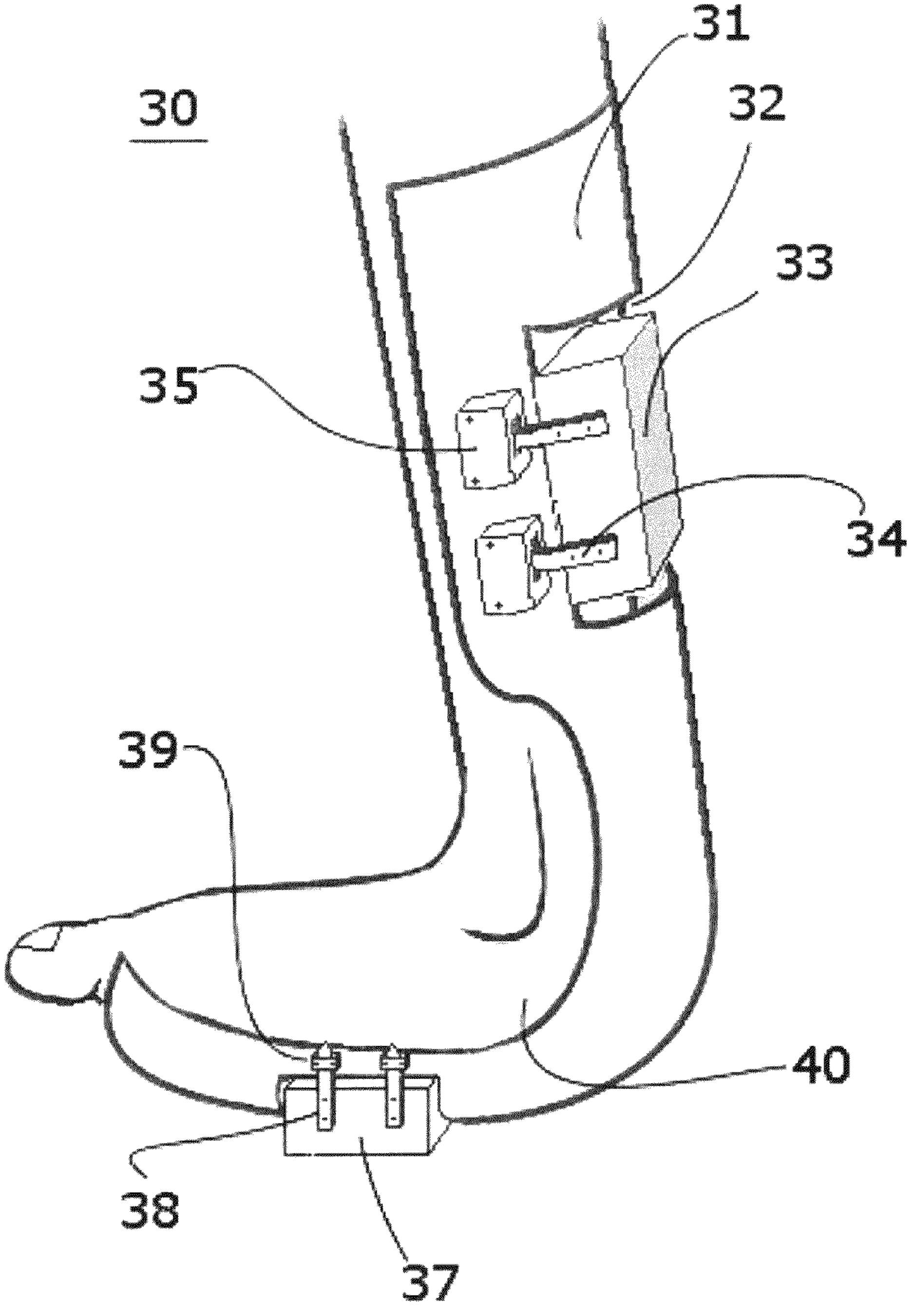
FIG. 7 is a schematic diagram that shows the device of FIG. 6 with a user's foot and ankle placed into the same limb engaging portion of the device.

FIGS. 5-7 depict another embodiment of the invention. Device 30 includes limb engaging portion 31 which is similar to a foot-ankle orthosis. In one embodiment, manipulator 33 is positioned adjacent location (A) to treat Achilles tendonitis. In a second embodiment, manipulator 37 is positioned adjacent location (B) to treat plantar fasciitis. For each embodiment, a window is made in limb engaging portion 31. It is recognized that both windows need not necessarily be configured into the same limb engaging portion 31.

FIG. 6 shows device 30 applied to the user's foot and ankle 40. The user places his or her foot and ankle 40 into device 30 to treat either Achilles tendonitis or plantar fasciitis. For treating Achilles tendonitis, window 32 exposes Achilles tendon 41, as shown in FIG. 6. Manipulator 33 can be affixed to limb engaging portion 31 by coupling structures 34 and paired receivers 35. Once manipulator 33 is affixed to limb engaging portion 31, the manipulator 33 can massage Achilles tendon 41 and its adjacent tissues to alleviate Achilles tendonitis.

For treating plantar fasciitis, window 36 in limb engaging portion 31 exposes sole 42 of foot 43. Manipulator 37 can be affixed to limb engaging portion 31 by virtue of coupling structures 38 and receivers 39. Once manipulator 37 is affixed to limb engaging portion 31, manipulator 37 can massage sole 42 of foot 43 and its adjacent tissues to alleviate plantar fasciitis. Bayonet-type mounting style is but only one embodiment for similarly mating two such structures, it will be appreciated that a variety of other mounts known to one skilled in the mechanical arts can be used. Also, straps affixed to the limb engaging portion of the device may be employed to immobilize a user's foot and ankle in the device. For clarity and brevity, the straps have been omitted from these drawings, but one of many restraining methods, such as hook-and-loop (VELCRO®) can be employed, and such strapping methods are common in the field of orthopaedic immobilization. Other alternative restraining means can be employed, such as a clamshell design with mechanical, zipper, or magnetic fastener or any other means that is obvious to others skilled in the art.

FIG. 7 illustrates manipulator 33 and manipulator 37 affixed to limb engaging portion 31 of device 30 by respective coupling structures 34,38 and receivers 35,39. To treat Achilles tendonitis, the foot and ankle 40 are immobilized. Manipulator 33, by being mounted at window 32, can massage the Achilles tendon and the surrounding tissues for as long as required. After massage treatment, manipulator 33 and/or manipulator 37 can be removed from limb engaging portion 31 of device 30. The user can continue to wear limb engaging portion 31 to allow foot and ankle 40 to rest for as long as is needed while still maintaining immobilization of the limb. As in previous figures, additional immobilization straps are not depicted, nor are any other mounting styles to affix the massaging portion to the limb engaging portion.

Figure 8:
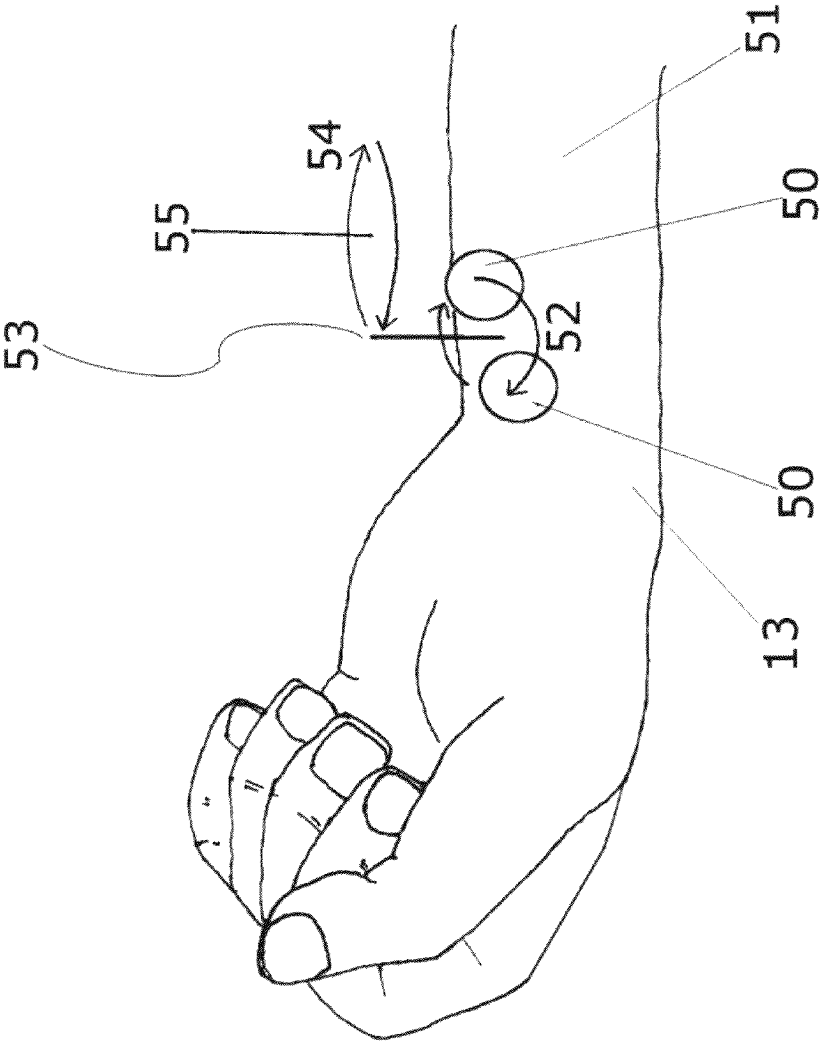
FIG. 8 is a schematic diagram illustrating motion of manipulating heads of the manipulator.

FIG. 8 depicts the functional mechanics inside manipulator 27 as it applies to the embodiment for treating carpal tunnel syndrome. Wrist 13, when held by the limb engaging portion (not shown) can be massaged by manipulator 27. The housing and mechanical components of manipulator 27 are not shown. Manipulator 27 can include one or more manipulating heads 50. Manipulating heads 50 can be spherical or hemispherical, wherein the rounded portion of the hemisphere contacts the user's skin area 51. Heads 50 rotate in the direction of arrow 52 about a central axis 53, which is substantially a common shaft from a geared assembly (not shown). Heads 50 also orbit about central axis 55 in the direction of arrow 54. Orbital motion can be achieved by using two or more gears from central axis 53 or 55 through which a gearmotor shaft (not shown) rotates. Those components not shown are omitted for clarity and brevity. Any person skilled in the mechanical arts may duplicate those functional requirements in any number of ways. While it is recognized that minimally one or two gears may be used to achieve orbital motion, such motion may be achieved in a number of ways that are known to one skilled in the mechanical arts. Other patterns of movement of the manipulating head or heads can be employed with corresponding mechanical means such as gears, levers, and other components that are known to those skilled in the art, and according to best practices of contemporary massage therapy.

Figure 9:
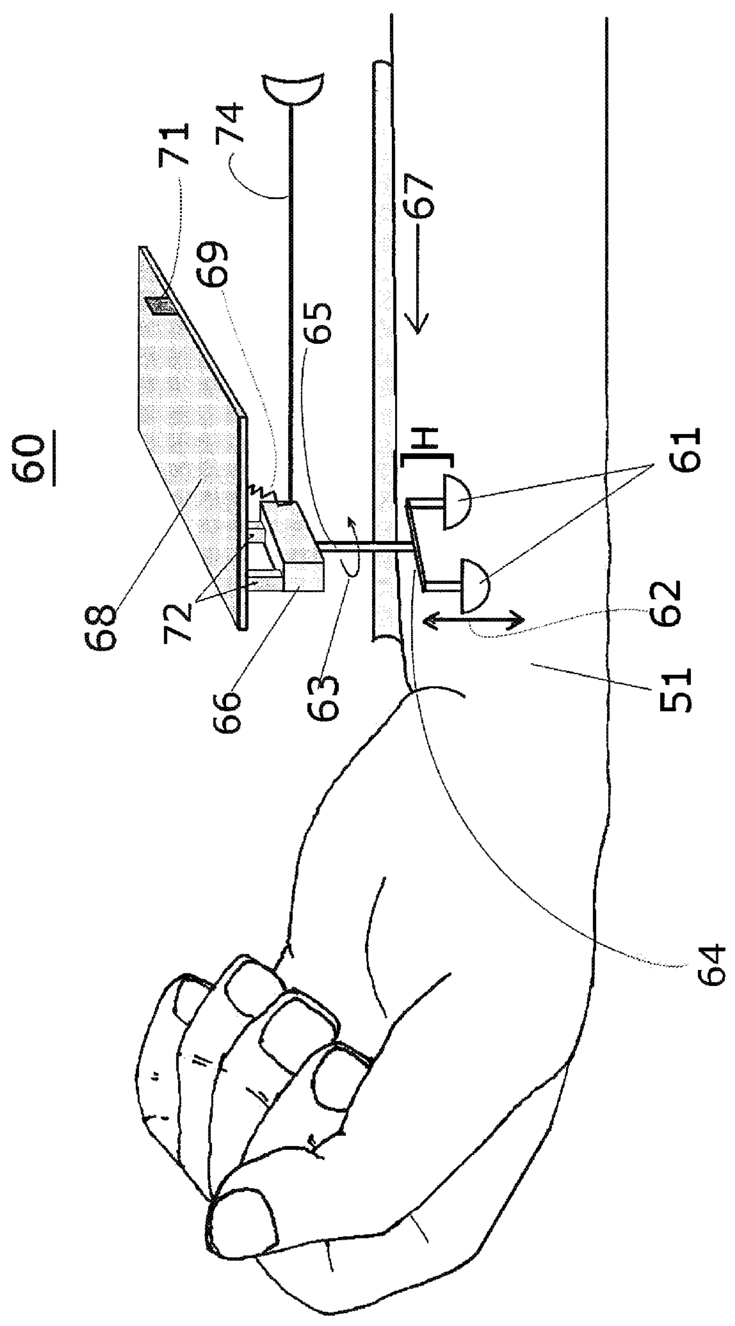
FIG. 9 is a schematic diagram in which a pair of manipulating heads of the manipulator can increase or decrease in height from the skin.

FIG. 9 demonstrates an embodiment of the invention where device 60 includes a pair of manipulating heads 61 of manipulator 67 coupled to housing 68. Manipulating heads 61 can increase or decrease height H, as indicated by double arrow 62, as they traverse over user's skin 51, and particularly over the uneven contours overlying a tendinous area. For the purposes of clarity, only rotational motion in the direction of arrow 63 of manipulating heads 61 is depicted, although either orbital or rotational motion is acceptable and can be used for massage therapy in this device. Such motion is achieved by manipulating heads 61 being attached to connectors 64. Connectors 64 are coupled or integral with central shaft 65 of gearmotor 66. Gearmotor 66 provides the orbital or rotational motion desired. Gearmotor 66 is suspended inside motor housing 68. For clarity, only the upper portion of motor housing 68 is depicted. The suspension of motor housing 68 to gearmotor 66 facilitates the floating of manipulating heads 61 above skin 51 which increases or decreases their height H over the skin's contours.

Depicted as only two means of the suspension only, and recognized as not being the only means to achieve the result of floating the heads above the skin, the two types of suspension mechanisms also provide flexibility of movement between manipulating heads 61 and motor housing 68. The first method uses a spring or springs 69, fastened between motor housing 68 or any other structure rigidly fixed to the motor. In a second method, one or more blocks of foam rubber 72 are affixed between gearmotor 66 and motor housing 68. It will be appreciated that such freedom of motion may be achieved by any number of mechanical means, and such means as known to one skilled in the art of mechanical transmission of power and motion. Any number of mechanical means may be used to suspend the motor and rotating heads above the surface of the wrist in order to provide massage. As described, the rotating heads need not be spheres, but must have substantially hemispherical surfaces for wrist contact in order to provide easy gliding of the heads over the skin and to avoid skin irritation. The heads translate, rotate, angle, and/or vibrate with respect to one another by virtue of their mutual attachment and their combined attachment to the gearmotor.

In order to provide more effective manipulation of the tendons by the manipulating head or heads, the inventors have found that flexing the tendons causes them to protrude above their planar surface at rest, and therefore provides a more suitable surface area for massage.

Suitably, the device contains electrical jack 74 connected to gearmotor 66. Power to gearmotor 66 can be provided by wall current (e.g., via a transformer in the case of a DC gearmotor) when an electrical plug is inserted into jack 74. Switch 71 can be located on manipulator 67 which can be used to activate/deactivate the device.

In the particular embodiments described above, power is provided by an external DC power source (not shown). However, in alternative preferred embodiments, a portable power supply, suitably a battery, is provided in the device which obviates the need for power wires.

Rotation of the motor shaft produces a cyclic orbital motion in the manipulating heads causing a lateral, longitudinal, and up-and-down massaging motions on the skin. The entire gearmotor assembly, inside the motor housing of the massage portion, can be constructed so as to slide cyclically, distally and proximally, on the limb. The drive mechanism for this movement can be produced by a method of dual motion that may be achieved by any number of mechanical means, and such means are known to one skilled in the art of mechanical transmission of power and motion. These methods include, but are not limited to, direct drive means, geared means or other mechanical means, any and all of which are known to one skilled in the art of mechanical transmission of power and motion.

For most practical applications, the gearmotor for the desired orbital massaging effect rotates the manipulating head or heads 61 at a rate of between 10 and 100 cycles per minute. It is recognized, however, that slower or faster cyclic rates can be used to achieve a desired symptomatic relief, depending on the body tissue to be massaged and the degree and/or type of dysfunction in that tissue. It has been found that if the device cycles with two manipulating heads 61 at a rate of 30-40 cycles per minute, and is used for 10 to 15 minutes twice a day by a sufferer of carpal tunnel syndrome or wrist flexor tendonitis for two weeks and then once a day for 10 to 15 minutes for a further one or two weeks, followed by several 10 to 15 minute sessions per week thereafter, significant improvements can be obtained. In particular, a significant reduction in hand pain is achievable.

The inventors have found that in embodiments of the present invention, manipulation of the tissue of the anterior wrist produces suppleness of the tissues. This in turn has been found to alleviate pain and other symptoms of carpal tunnel syndrome, wrist flexor tendonitis and wrist flexor tenosynovitis.

The inventors consider manipulation of the tendons, and in particular the wrist flexor tendons, as causing the tendons to become more supple, with fewer adhesions to bind them to adjacent tissues. Further, blood flow is likely stimulated which accelerates the restorative process. Also, the tendons are likely to become less inflamed since the manipulation will enhance interstitial fluid drainage. In addition, reduced inflammation of the tendons is likely to occur and this would impart a smaller cross sectional area inside their respective tendon sheaths within the carpal tunnel. Such would discourage further adhesion formation and allow for more effective tendon gliding inside the sheath in the carpal tunnel. Also, creating a smaller tendon cross sectional area will provide more room inside the carpal tunnel thereby relieving pressure on the median nerve and concomitant pain and other symptoms therefrom.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

The invention claimed is:

1. A device for manipulating one or more tendons in the wrist, elbow, knee, shoulder, plantar fascia or Achilles tendon region, the device comprising a limb engaging portion; and a manipulator removably coupled to the limb engaging portion, the manipulator comprises at least one manipulating head and driving means for driving the at least one manipulating head, the at least one manipulating head being coupled to the driving means and driven by the driving means so as to provide the manipulation, the at least one manipulating head comprises at least one pair of massaging elements, balls or rollers spaced from and on opposite sides of a shaft, said shaft is configured to either rotate or orbit the at least one pair of massaging elements, balls or rollers on the surface of the skin over the tendons, the at least one manipulating head being suspended from a housing, the at least one manipulating heads configured to increase or decrease in height as the device moves on the surface of the skin over the tendons, wherein the manipulator is adapted to be located adjacent to the skin and move against the skin to manipulate the tendons below the skin and the manipulator is configured to provide three dimensional massage motion comprising of co-planar lateral, co-planar horizontal, and substantially perpendicular with respect to the surface of the skin; and wherein the driving means include a gearmotor suspended inside a motor housing by springs fastened between the motor housing and the gearmotor.

2. The device according to claim 1, wherein the limb engaging portion is rigid, and the manipulator is an electromechanical manipulator.

3. The device according to claim 1, wherein the limb engaging portion contains an opening or window, the manipulator being removably coupled over the opening or window and the opening or window being adapted to be placed over body tissue of the one or more tendons.

4. The device according to claim 1, wherein the limb engaging portion and the manipulator together provide massage therapy and the manipulator can be removed from the limb engaging portion.

5. The device according to claim 1 wherein the manipulator can move proximally, transversely, and distally along the skin.

6. The device according to claim 1 wherein manipulator comprises one or more head or heads wherein the one or more heads rotate repeatedly.

7. The device according to claim 1, wherein the manipulator provides rotational, lateral, longitudinal, vertical, vibrational or orbital motion for massaging across the tendons.

8. The device according to claim 1, wherein the limb engaging portion includes a joint hinging two portions of the limb engaging portion on either side of the joint for either extending or flexing a joint of a limb thereby extending the one or more tendons and/or causing the one or more tendons to protrude.

9. The device according to claim 8, wherein the one or more tendons is a flexor or extensor tendon.

10. The device according to claim 8, wherein the joint is locked into a particular angle or position.

11. The device according to claim 1, wherein the limb engaging portion is adapted to restrain a limb and substantially immobilize the limb when the device is in use.

12. The device according to claim 1, wherein the limb engaging portion is adjustable to accommodate different limb sizes.

13. The device according to claim 1, wherein the limb engaging portion comprises at least one adjustable strap.

14. The device according to claim 1, wherein the device includes a protective layer associated with the manipulator, the protective layer is configured to be located between the manipulator and the skin.

15. The device according to claim 1, wherein the manipulator includes a motor.

16. The device according to claim 1, wherein the device is portable.

17. A device according to claim 1, wherein the device includes a battery, the battery being connectable to the manipulator.

18. The device according to claim 1, wherein the device comprises a protective layer located so that the protective layer is configured to be adjacent to the skin during use.

19. The device of claim 1 further wherein said at least one pair of massaging elements, balls or rollers are attached to connectors, the connectors are coupled or integral with said shaft, said shaft being part of said gearmotor.

20. The device of claim 19 wherein said gearmotor is suspended with one or more foam rubber blocks affixed between said gearmotor and said motor housing.

21. A method for manipulating one or more tendons in the wrist, elbow, knee, shoulder, plantar fascia or Achilles tendon region comprising the steps of:

attaching a limb engaging portion to a limb including the one or more tendons; and manipulating the one or more tendons with a manipulator removably coupled to the limb engaging portion, the manipulator comprises at least one manipulating head and driving means for driving the at least one manipulating head, the at least one manipulating head being coupled to the driving means and driven by the driving means so as to provide the manipulation, the at least one manipulating head comprises at least one pair of massaging elements, balls or rollers spaced from and on opposite sides of a shaft, said shaft is configured to either rotate or orbit the at least one pair of massaging elements, balls or rollers on the surface of the skin over the tendons, the at least one manipulating head being suspended from a motor housing, the at least one manipulating head configured to increase or decrease in height as the device moves on the surface of the skin over the tendon;

wherein the manipulator is adapted to be located adjacent to the skin and moves against the skin to manipulate the one or more tendons below the skin; and wherein the driving means include a gearmotor suspended inside said motor housing by springs fastened between the motor housing and the gearmotor.

22. The method according to claim 21, wherein the method further comprises the step of:

adjusting the limb engaging portion to restrain the limb before the manipulating step.

23. The method according to claim 21, wherein the method further comprises the step of:

extending the one or more tendons and/or causing the one or more tendons to protrude from the joint before the step of manipulating the one or more tendons.

24. A method of treating or alleviating symptoms of carpal tunnel syndrome, the method comprising the steps of:

attaching a limb engaging portion to a limb including one or more tendons;

manipulating the one or more tendons in the anterior wrist with a manipulator by providing a lateral, proximal, distal motion and orbital motion to the one or more tendons with respect to the anterior wrist, the manipulator comprises at least one manipulating head and driving means for driving the at least one manipulating head, the at least one manipulating head being coupled to the driving means and driven by the driving means so as to provide the manipulation, the at least one manipulating head comprises at least one pair of massaging elements, balls or rollers spaced from and on opposite sides of a shaft, said shaft is configured to either rotate or orbit the at least one pair of massaging elements, balls or rollers on the surface of the skin over the tendons, the at least one manipulating head being suspended from a motor housing, the at least one manipulating head configured to increase or decrease in height as the device moves on the surface of the skin; and wherein the driving means include a gearmotor suspended inside said motor housing by springs fastened between the motor housing and the gearmotor over the tendons.

25. A method of treating or alleviating the symptoms of carpal tunnel syndrome, wrist tenosynovitis and tendonitis, cubital tunnel syndrome, neck tendonitis, plantar fasciitis, and Achilles tendonitis the method comprising the steps of:

attaching a limb engaging portion to a limb affected by carpal tunnel syndrome, wrist tenosynovitis and tendonitis, cubital tunnel syndrome, neck tendonitis, plantar fasciitis, and Achilles tendonitis, the limb including one or more tendons; and manipulating the one or more tendons with a manipulator removably coupled to the limb engaging portion, the manipulator comprises at least one manipulating head and driving means for driving the at least one manipulating head, the at least one manipulating head being coupled to the driving means and driven by the driving means so as to provide the manipulation, the at least one manipulating head comprises at least one pair of massaging elements, balls or rollers spaced from and on opposite sides of a shaft, said shaft is configured to either rotate or orbit the at least one pair of massaging elements, balls or rollers on the surface of the skin over the tendons, the at least one manipulating head being suspended from a housing, the at least one manipulating heads configured to increase or decrease in height as the device moves on the surface of the skin over the tendons, wherein the manipulator is adapted to be located adjacent to the skin and moves against the skin to manipulate the one or more tendons below the skin; and wherein the driving means include a gearmotor suspended inside said motor housing by springs fastened between the motor housing and the gearmotor.

* * * * *